United States Patent [19]

Carduck et al.

[11] 4,185,025

[45] Jan. 22, 1980

[54] CONTINUOUS PROCESS FOR OZONIZING UNSATURATED COMPOUNDS

[75] Inventors: Franz-Josef Carduck, Haan; Axel Dräger, Düsseldorf; Gunter Effey, Monheim; Suresh Majmudar, Haan; Martin Witthaus, Dusseldorf, all of Fed. Rep. of Germany

[73] Assignee: Henkel Kommanditgesellschaft auf Aktien (Henkel KGaA), Dusseldorf-Holthausen, Fed. Rep. of Germany

[21] Appl. No.: 966,948

[22] Filed: Dec. 6, 1978

Related U.S. Application Data

[63] Continuation-in-part of Ser. No. 888,528, Mar. 21, 1978, abandoned.

[30] Foreign Application Priority Data

Dec. 7, 1977 [DE] Fed. Rep. of Germany ....... 2754366

[51] Int. Cl.$^2$ ............................ C09F 7/02; C11C 3/00
[52] U.S. Cl. .................................... 260/406; 260/413; 562/571; 422/189; 422/190; 422/191; 422/194; 422/224
[58] Field of Search ...................... 260/406, 413 R; 562/571

[56] References Cited

U.S. PATENT DOCUMENTS 2,813,113  11/1957  Goebel .................................. 260/406
2,865,937  12/1958  Maggiolo ............................. 260/406

OTHER PUBLICATIONS

Nandet, M. et al. Chem. Absts., vol. 79, No. 104702c (1973).
Yurlev, Y. et al. Chem. Absts., vol. 77, No 33967p (1972).
Gel'Chenok, N. et al. Chem. Absts., vol. 81, No. 90643m (1974).

*Primary Examiner*—John F. Niebling
*Attorney, Agent, or Firm*—Hammond & Littell

[57] ABSTRACT

A process and an apparatus for the continuous ozonization of unsaturated organic compounds in the presence of water, wherein (a) the fresh charge mixture of unsaturated compounds to be ozonized is reacted in at least one first reactor in parallel flow with ozonic gas, which was previously used for ozonizing a previously partially ozonized charge mixture, and (b) simultaneously a previously partially ozonized charge mixture is reacted in at least one second reactor in parallel flow with fresh ozonic gas, and wherein, optionally, said at least two reactors contain at least two mixing sections for mixing the charged liquid and gaseous phases with each other where the hydraulic diameter of the mixing elements in the individual mixing section is reduced in the flow direction.

11 Claims, 6 Drawing Figures

CONTINUOUS PROCESS FOR OZONIZING UNSATURATED COMPOUNDS

REFERENCE TO PRIOR APPLICATIONS

This application is a continuation-in-part of Patent Application Ser. No. 888,528, filed Mar. 21, 1978, and now abandoned.

FIELD OF THE INVENTION

The invention relates to a process and device for the continuous ozonizing of unsaturated compounds, specifically of long-chain and/or high-molecular weight compounds, such as olefins, oleic acid or linoleic acid, in the presence of water.

BACKGROUND OF THE INVENTION

By ozoning (through ozone addition), long-chain, unsaturated compounds, ozonized products, specifically ozonides, can be manufactured, which can be subsequently cleaved into shorter chain fragments. Depending upon the type of ozonized product and the cleavage process, oxidative or reductive, the latter shorter chain fragments consist primarily of acids, aldehydes, ketones of alcohols. If, for example, commercial oleic acid (from olein) is treated with ozone, the ozonide produced decomposes exothermally (by adding oxygen) into pelargonic acid and azelaic acid. If olefins are ozonized, then on oxidative cleaving corresponding carboxylic acids and carbonyl compounds, and on reductive cleaving alcohols and carbonyl compounds, are produced.

The present invention applies to the ozonizing of unsaturated compounds, specifically olefins, including unsaturated carboxylic acids, with both one and more than one double bond. The process according to the invention and the device for implementing the process, however, do not cover the cleaving of the ozonized product. This cleavage step in any given case is the subject of a subsequent processing step and/or system.

The ozonization of unsaturated compounds can be described by the following reaction:

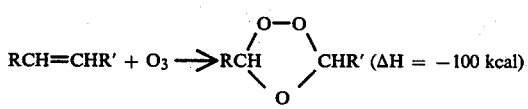
(1) $\Delta H = -100$ kcal

The reactive enthalpy ($\Delta H$) of this ozonizing reaction amounts to about 100 kcal/mol of double bonds or about 2,000 kcal/kg of reacted ozone. The elimination of this large amount of heat creates a great problem since the reaction is supposed to take place at a relatively low temperature in order to prevent a premature onset of ozonide cleaving. Ozonides are relatively unstable and already start to decompose at room temperature—this step equally being an exothermal reaction.

As mentioned, the ozonized product, in this case the ozonide, is cleaved only in a subsequent step. The splitting can be accomplished, e.g., oxidatively at about 100° C., according to the following reaction:

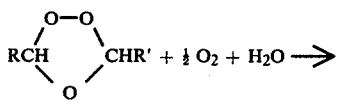
(2)

-continued
RCOOH + R' COOH + H$_2$O

To prevent a premature onset of this cleavage of the ozonide, a reactive solvent can be added to reaction (1), for example, an organic acid or alcohol, which converts ozonides to ester hydroperoxides and/or alkoxy hydroperoxides, which in turn are substantially more stable than the ozonides themselves. In the former case, e.g., the following reaction takes place:

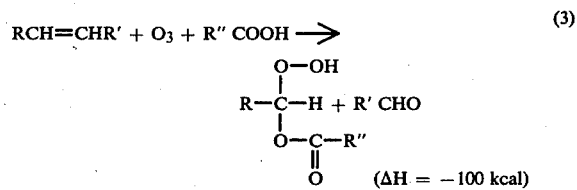
(3) ($\Delta H = -100$ kcal)

The resulting ozonized products produced, in this case ester hydroperoxides and aldehydes, can be subsequently converted in a separate reaction step to corresponding acids by hydrolytic-oxidative fission.

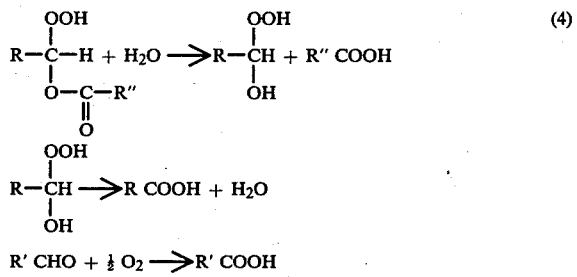
(4)

After separation by distillation, the reactive solvent (R" COOH) can be returned to the process.

An effect of ozonization is that the viscosity of the ozonized product is considerably increased. The viscosity can be reduced, however, by the reactive solvent used for stabilization in reaction (3). U.S. Pat. No. 2,813,113, for example, teaches that in the ozonolysis of oleic acid the viscosity of the liquid phase in the ozonization reaction is reduced by adding pelargonic acid to the charge mixture. Following the oxidative splitting of the ozonide, both the added and the produced pelargonic acid are separated from the manufactured azelaic acid.

Aside from the problem of keeping the viscosity of the ozonized product at a low level, there is the requirement, as mentioned above, of removing the heat of reaction of the ozonization reaction, at least to the extent that the cleavage of the ozonized product, for example, the ozonide or ester hydroperoxide, is sufficiently delayed. For this purpose the reaction temperature, if possible, should not exceed about 50° C.

To carry off the heat of the reaction by evaporation cooling means, it was proposed in U.S. Pat. No. 2,865,937 that from 100% to 600% of water be added to the organic charge mixture. The reaction heat is then eliminated by water evaporation and by the removal of water vapor together with waste gases. However, by means of the reaction heat, only about 4 kg of water per kg of reacted ozone are evaporated. The remaining water stays with the ozonized product and has to be evaporated at considerable expense. The problem is compounded by the fact that the specifically short-chain reaction products are volatile in the presence of water vapor. This produces not only a loss of acceptable products, but makes for additional air exhaust and/or waste water problems. Furthermore, according to data given in U.S. Pat. No. 2,813,113, the presence of a substantial volume of water (exceeding 10% to 15%) will have a negative effect on the ozonized product.

However, if the reaction heat is to be removed by indirect cooling according to U.S. Pat. No. 2,813,113, then because of the required low temperature of 25° to 45° C., a high expense in equipment, together with the high power and coolant water requirements, are needed for the removal of reaction heat.

Both for economic and engineering reasons a practically quantitative conversion of reactants is a basic requirement in the ozonization process. Primarily because of the danger of air pollution and the poisonous nature of ozone—the maximally tolerable working place concentration (MAC)=0.1 ppm—the entire quantity of ozone employed in the reaction should be used up to prevent it from being exhausted into the open air together with the waste gases. Otherwise, extensive ozone disposal installations would be required. Therefore, according to the known process of U.S. Pat. No. 2,813,113, a counterflow reactor is proposed, in which the liquid phase flows from top to bottom and the ozone containing gas from the bottom to the top. However, a counterflow reactor is very expensive for ozonizing because of the large gas-liquid ratio and the high viscosity of the ozonized product. Contrasted with such a counterflow reactor, a parallel or concurrent flow operation would make it feasible to allow a 20- to 30- fold greater gas velocity in the reactor, so that the latter paralleled flow reactor could be designed on a correspondingly smaller scale. But up until now no quantitative conversion of reactants has been successfully carried out with a parallel flow operation.

OBJECTS OF THE INVENTION

An object of the invention is to provide a process and apparatus for the ozonization of unsaturated organic compounds which without an expensive counterflow operation in the reactor results in a practically quantitative conversion of the ozonizing charge mixture with a minor, not more than negligible, excess of ozone.

Another object of the invention is to provide an apparatus for the ozonization of unsaturated organic compounds, consisting of two or more concurrent flow reactors of relatively small size, with the individual reactors being interconnected in a counterflow arrangement, thus providing a means for attaining an almost quantitative conversion within very narrow limits in continuously self-regulating way.

An additional object of the invention is to provide a process and apparatus for the ozonization of unsaturated organic compounds in which the ozonic charge has a relatively low ozone concentration but the reactor's dimensions are still relatively small.

A further object of the invention is to provide a process and apparatus for the ozonization of unsaturated organic compounds in which concurrent flow reactors are provided with static mixer elements, which ensure an intensive mixing of reactants and reaction products, thus promoting temperature control, high reaction velocity and safety and economy of operation.

Another object of the invention is to provide a process for the continuous ozonization of unsaturated compounds, more particularly of long-chain and/or high-molecular weight compounds, such as olefins, oleic acid or linoleic acid, etc. in the presence of water, in which (a) the fresh charge mixture to be ozonized is reacted in parallel flow with ozonic gas, which previously was used for ozonizing an already partially ozonized charge mixture, and (b) simultaneously an already partially ozonized charge mixture is reacted in parallel flow with fresh ozonic gas.

A still further object of the invention is to provide an apparatus for the continuous ozonization of unsaturated compounds, more particularly of long-chain and/or high-molecular weight compounds, such as olefins, oleic acid or linoleic acid, etc. in the presence of water, in which a reactor system is provided having at least two reactors which are connected in a counterflow arrangement, but through which the charge mixture to be ozonized and the ozonic gas pass in parallel flow.

A yet further object of the present invention is to provide, in the at least two reactors, mixing sections containing static mixing elements for mixing the charge phases with one another and with the reaction products where the said static mixing elements of the individual mixing sections have varied hydraulic diameters and the mixing sections are arranged whereby a reduced hydraulic diameter of the static mixing elements occur in the direction of the parallel flow.

These and other objects of the present invention will become more apparent as the description thereof proceeds.

THE DRAWINGS

DESCRIPTION OF THE INVENTION

Figure 1:
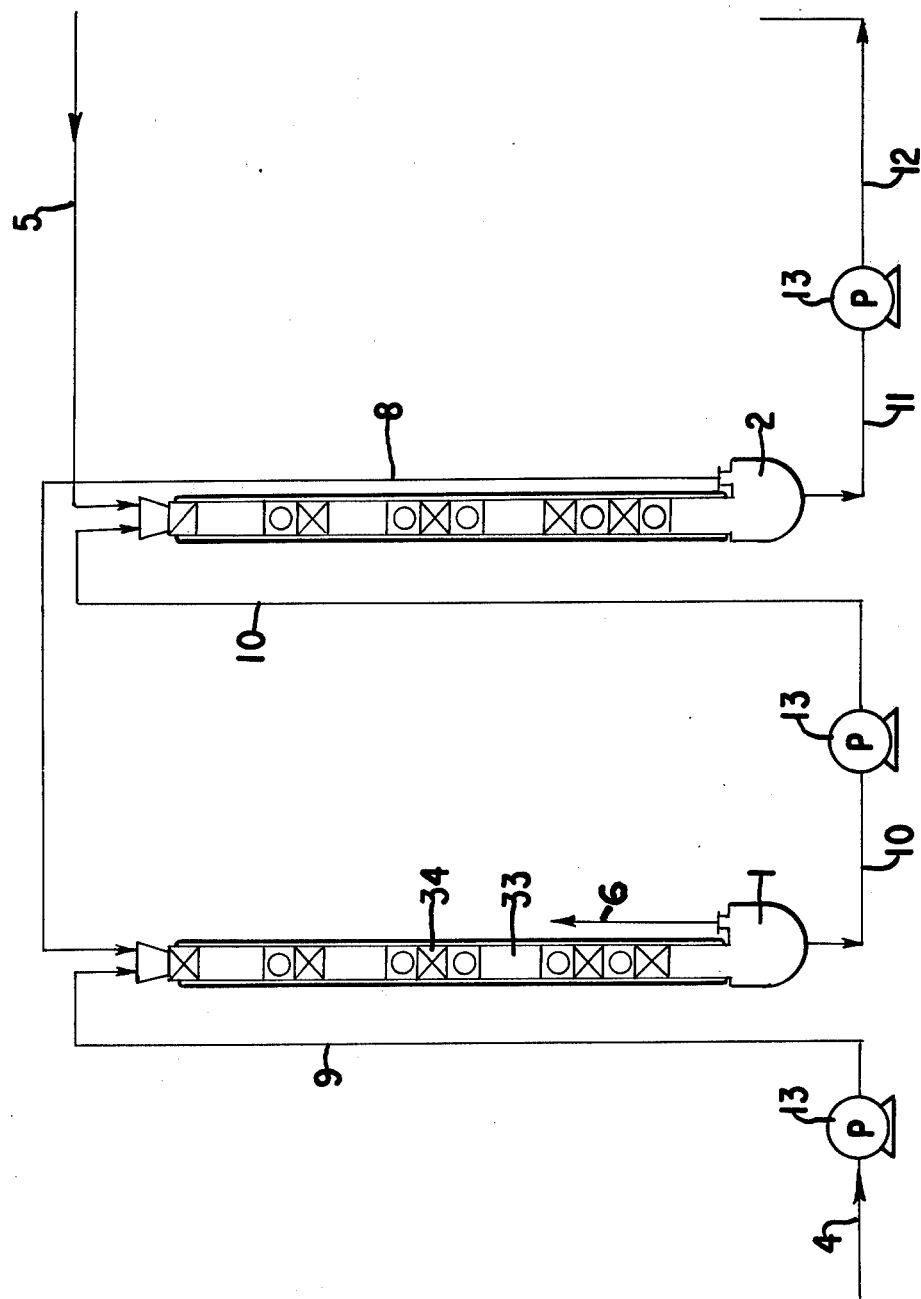
FIG. 1 is a diagrammatic flow chart indicating two reactors, pumps and the material flow.

The objects of the invention have been achieved and the drawbacks of the prior art have been overcome by the development of a process for the continuous ozonization of unsaturated compounds, in particular of long-chain and/or high-molecular weight unsaturated compounds, such as olefins, oleic acid, linoleic acid, etc. in the presence of water, wherein:

(a) a fresh charge mixture to be ozonized, which contains said unsaturated compounds, is reacted in parallel flow with ozonic gas, said ozonic gas having been previously used for ozonizing a previously partially ozonized charge mixture, and (b) simultaneously a previously partially ozonized charge mixture is reacted in parallel flow with fresh ozonic gas.

The invention also provides an apparatus for the continuous ozonization of unsaturated compounds, in particular of long-chain and/or high-molecular weight unsaturated compounds, such as olefins, oleic acid, linoleic acid, etc. in the presence of water, in which a reactor system is provided having at least two reactors which are connected in a counterflow arrangement with respect to each other but through each of which individually the charge mixture to be ozonized and the ozonic gas pass in parallel flow.

According to the invention, both of the reactants, consisting on the one hand of an organic charge mixture to be ozonized, which preferably contains 2 to 49 by weight percent of water, based on the total weight of the charge mixture, and on the other hand of ozonic gas, are fed in parallel flow through at least two counterflow-connected reactors of a reactor system. Reactants and reaction products are thereby constantly and intensively mixed in the reactors under in-situ evaporative cooling conditions for the control of ozonization and the uniform removal of reaction enthalpy. A simultaneous outer counterflow operation and inner parallel flow operation with a reactor system consisting of at least two reactors is so accomplished that the charging mixture to be ozonized is fed to the reactor system from one side while the ozonic gas is fed in from the other side, so that although the reactants flow through the reactors in a counter cycle, they flow through each single reactor in the same direction.

With respect to the required water content of 2% to 49% by weight of the charge mixture to be ozonized, at least so much water is to be charged as is required for the in-situ removal of ozonization related reaction enthalpy. Preferably, the water required additionally for the subsequent hydrolytic-oxidative scission is also initially added to the charge mixture (organic phase) to be ozonized.

More particularly, the present invention relates to a continuous process for the ozonization of higher molecular weight olefinically unsaturated organic compound which consists essentially of the steps of:

(a) continuously feeding a fresh charge mixture of the unsaturated organic compound, said compound having a boiling point at normal pressure of at least 50° C., which mixture contains 2 to 49 weight percent of water, relative to the weight of said unsaturated organic compound, into parallel flow in a confined space with the ozone-containing off gas from a previous ozonization wherein said unsaturated organic compound and said ozone-containing off gas are intimately mixed continuously throughout their parallel flow together and wherein the partially ozonized charge produced is optionally similarly reacted with a further charge of ozone-containing gas in one or more additional parallel flow reactions, (b) continuously withdrawing from step (a) a partially ozonized charge and gas substantially free of ozone, (c) continuously feeding said partially ozonized charge containing water from step (b) into parallel flow in a confined space with ozone-containing gas and intimately mixing said partially ozonized charge and said ozone-containing gas continuously throughout their parallel flow together, (d) continuously passing ozone-containing gas containing 0.1 to 1 volume percent ozone into step (c), (e) continuously withdrawing the ozonized charge containing none-to-sufficient water for hydrolysis of the ozonide and a partially depleted ozone-containing off gas, (f) continuously separating said gas, and cycling it to step (a), and (g) continuously recovering an ozonide of said higher molecular weight olefinically unsaturated organic compound, and wherein said parallel flow reactions in steps (a) and (c) are conducted at a predetermined temperature of from 10° to 50° C. and at a pressure sufficient that substantially all the heat of reaction is removed by evaporation of the water present.

The advantageous result of the invention is that the ozonization operation which involves products of a relatively high viscosity is feasible with reactors of relatively small dimensions by using a reactor system consisting of two or more parallel flow reactors, in which the individual reactors are interconnected in a counter-flow arrangement. This operating mode and/or corresponding apparatus result, if so required, in an almost quantitative conversion of the reactants, namely, of the charge mixture to be ozonized and the ozone.

The reaction temperature can simultaneously be kept within very narrow limits in a constantly self-regulating way by in-situ evaporative cooling without any additional indirect cooling. The equilibrium temperature for any given reaction mixture is thereby substantially determined by the ozone concentration.

Ozone, as is well known, is produced by silent electrical discharges. Current consumption amounts to approximately 18 to 25 kWh/kg ozone, if air is used as oxygen source. The lower the ozone concentration in the ozonized air, the lower is the specific current consumption. Even with a reduction of the ozone concentration in the air from 2% to 1%, the specific current consumption drops by about 30%. Therefore, from the standpoint of energy conservation, it pays to work with a lower ozone concentration. However, a lowering of the ozone concentration logically involves the manipulation of larger air volumes, i.e., with a conventional counterflow operation carried out in a column, very large column cross-sections would be required. Another advantage of the invention is that an air charge with a lower ozone concentration can be used and, despite this, the reactor dimensions can be kept relatively small, whereby both ozone and unsaturated compounds are for all practical purposes quantitatively converted.

In designing the apparatus, it must be taken into consideration that ozone-containing gas having an ozone concentration of only 0.5 to 2.5% by volume and an initial pressure, of as a rule, less than 2 bar is available, that the volume ratio of liquid phase to gas phase (in the process of the invention) is about 1:1,500 to 4,000, and that the viscosity increased with increasing degree of ozonization. It must be further considered that the reaction heat during ozonization is about 2,000 kcal/kg of ozone, but that the temperature in the reactor should be limited to 10° to 50° C., so that the ozonide cleaving will not occur prematurely.

Therefore, according to our invention, the reactors in the form of parallel or concurrent flow columns provided with static mixing elements of such a type and arrangement that a mixture of reactants, including water and reaction products, is ensured, the mixing of which mixture is intensified with an increasing degree of ozonization. Because of this intensive mixing of reactants and reaction products operations are feasible, in contrast, for example, to the case of U.S. Pat. No. 2,865,937, with a charge mixture (organic phase) which is only 2% to 49% by weight hydrous being ozonized at an always sufficiently low viscosity of the liquid phase. A further result is that the reactors do not have to be equipped throughout with such static mixing elements.

The static mixers (having non-moving parts) used according to the invention can be designed, for example, from individual mixing elements, which consist of corrugated lamellas, and which are so layered one upon the other that open, intersecting channels are produced. In said mixing elements the fluid is separated into individual currents. At each crossing point, a partial amount of the fluid is cut off into a crossing channel. The initial non-homogeneous condition is thus adjusted to a homogeneous state, two-dimensionally in the first mixing unit and in the following one, with a 90° rotation, three-dimensionally (see the prospectus of the firm Sulzer AG, Winterthur, Switzerland, No. 22.85.06-Cgc 40). However, other stationary mixing devices can also be used, as for instance, one such mixer which consists of a plurality of stationary elements or parts arranged in a tubular housing in a right- and left-hand pathway (spirals). During operation the medium to be mixed separates at the entry point of each mixing element into two partial streams and follows two semicircular channels. At the border of each subsequent mixing element, the two partial streams are again divided and simultaneously reunited with one of the partial streams from the oppositely positioned semicircular channel (see U.S. Pat. Nos. 3,286,992, 3,663,638 and 3,704,006). The teachings of these references with respect to the stationary mixing elements are incorporated herein by reference.

Experience has shown that the static or stationary components can be partially or entirely replaced by filter beds. Particularly well suited are those filter beds which, despite larger surfaces, do not have an emulsion breaking effect, do not permit small pools of liquid to form and have only a small hold-up effect. The column reactors could also be replaced by two tube bundle reactors which must then be equipped with corresponding filter beds or static mixing parts. In principle, all so-called static mixers can be employed.

It has been found, surprisingly, that the ratio of reaction heat being released, $Q_R$, to removable heat, $Q_A$, per unit of volume in a reaction tube of the apparatus of the invention depends on the hydraulic diameter of the static mixer inserts. Furthermore, this ratio is appreciably smaller in an empty tube (not containing mixing elements) than in a tube packed with filling bodies, etc. With the selection of suitable mixing elements by gradation of their hydraulic diameters, it is possible according to the invention to leave the ratio of $Q_R/Q_A$ at 1, so that the reaction can be conducted at almost constant temperature.

In a further aspect of the invention, the reaction can also be controlled in that there occurs in a unit volume of an equalization of the heat quantities $Q_R$ and $Q_A$, so that a mixing section with a ratio of $Q_R/Q_A > 1$ is followed by an empty space with $Q_R/Q_A < 1$. The unit of volume is to be selected so that a given maximum temperature is not exceeded in the section. This arrangement leads to reactors with shorter mixing sections and hence lower investments. The increasingly intensive mixing required by the increasing viscosity and decreasing conversion increment can advantageously be achieved by varying in a unit of volume the ratio of mixing section to empty tube section in favor of the mixing section, so that again an equalization of the heat quantities occurs.

According to a still further aspect of the invention, the latter can alternatively be achieved by reducing the hydraulic diameter of the filling bodies as the reaction proceeds, so that per unit volume of mixing section the conversion increment becomes the same and the ratio of mixing section to empty tube length remains unchanged.

The mixer inserts used according to the invention can be those described above, that is, for example, separate mixing elements, each of which consists of grooved laminations, and which are stacked so that open, intersecting channels are formed. In the latter the fluid is divided into separate streams. At each intersection a partial quantity is sheared off into the intersecting channel. An inhomogeneity is compensated in the first mixing element two-dimensionally and in the following, rotated by 90°, three-dimensionally. Instead of or in addition to these mixers with intersecting channels, other static mixers may alternatively be used, for example, that one discussed above consisting of a number of right-handed and left-handed elements (spirals) arranged stationary in a tube housing.

Details of the arrangement of mixing sections and empty spaces according to the invention as well as the type of mixer inserts were determined by experiments. For example, in a nested tube reactor with tubes of the dimensions 48.3 dia.×2, static mixing elements of the above-mentioned spiral type may in advantageous embodiment of the invention be used in the start-up section and in the subsequent mixing sections, the above-mentioned mixers with intersecting channels having hydraulic diameters of 8 and 4 mm, respectively, can be used. As sufficient for the solution of the problem underlying the invention, the value of 1:6 was determined for the ratio of total mixing length to empty length.

In the apparatus according to the invention, instead of or in addition to the static mixing elements containing regularly arranged filling bodies, random packed filling bodies may be used. Especially suitable to this end are filling bodies which despite a relatively large surface are not emulsion breaking, do not cause liquid nests to be formed, and have only a small hold-up.

According to the invention, both nested tube reactors and column reactors are usable. In both cases the reactors may be provided with cooling or heating jackets, making it possible in addition to adjust the equilibrium temperature which establishes itself due to the in situ evaporation-cooling, as needed, independently of the chosen ozone concentration and/or the chosen concentration of the unsaturated compounds in the charge mixture. Often, however, cooling or heating units will be less necessary in the apparatus according to the invention because here the desired equilibrium temperature is adjustable within sufficiently narrow limits already by the arrangement of mixing sections and empty spaces as well as the type of mixing inserts.

Figure 2:
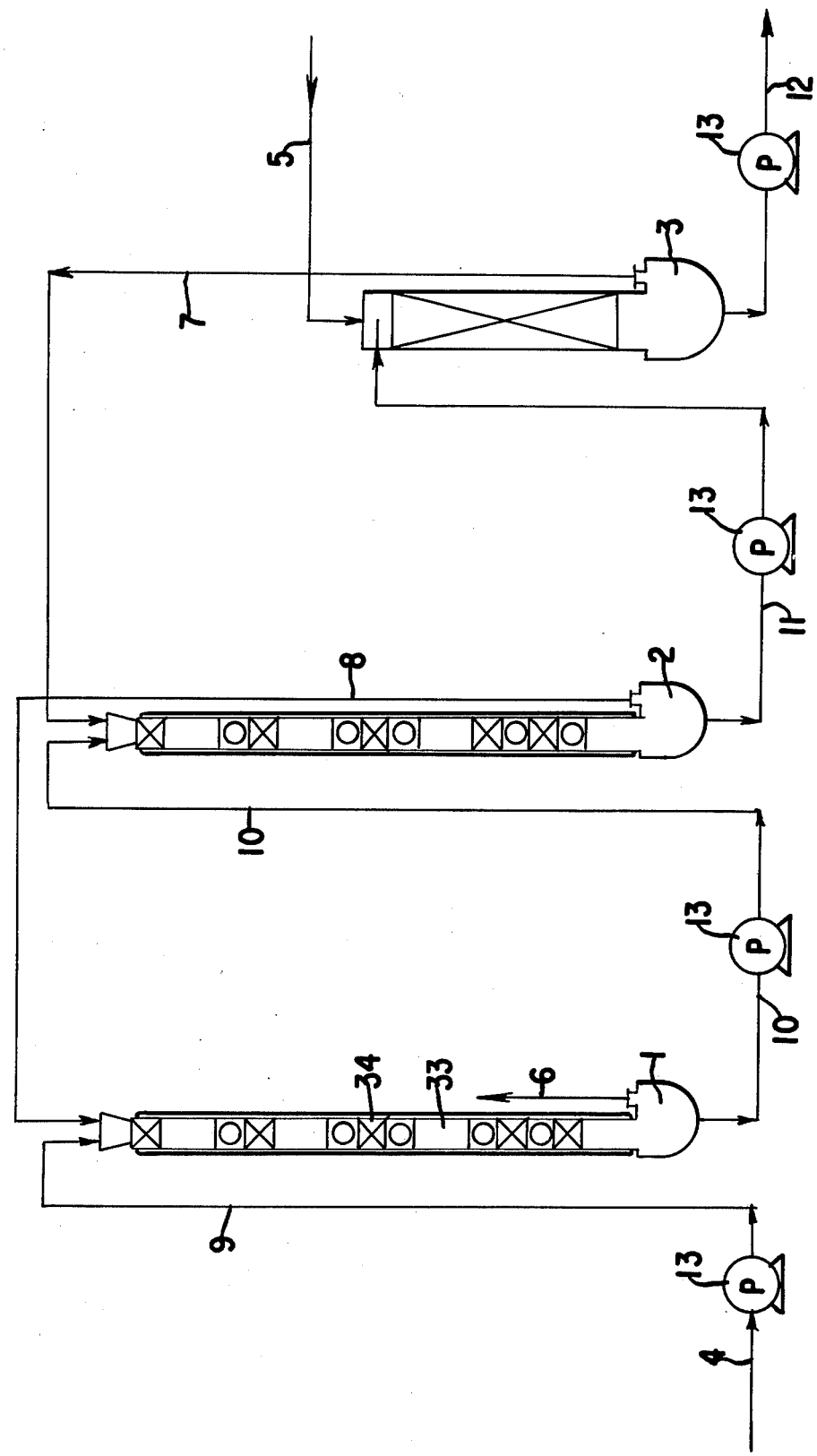
FIG. 2 is a diagrammatic flow chart indicating the two reactors of FIG. 1 and a booster reactor and pumps and the material flow.
Figure 3:
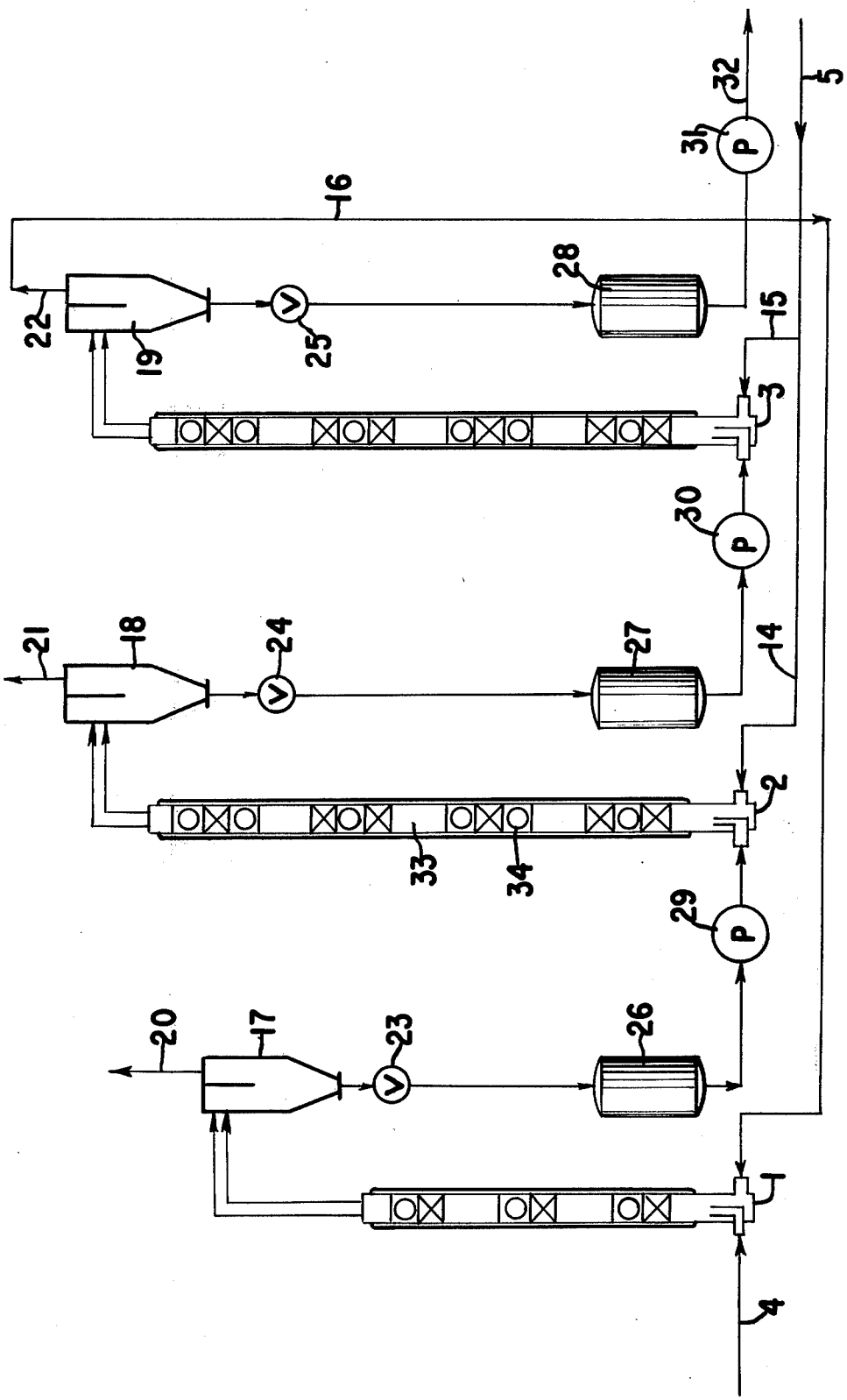
FIG. 3 is a diagrammatic flow chart indicating three reactors together with intermediate tanks, valves and pumps and the material flow.
Figure 6:
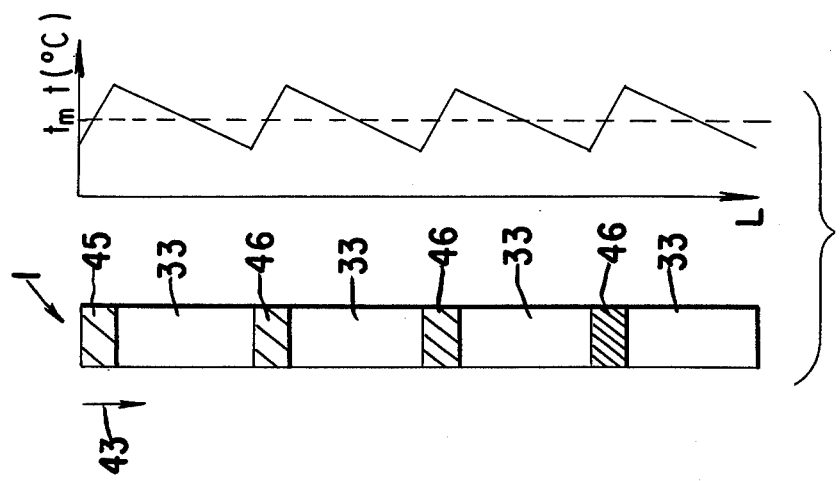
FIG. 6 is a cross-section of a reactor with mixing sections of graded hydraulic diameter with a constant ratio of mixing sections to empty spaces.
Figure 5:
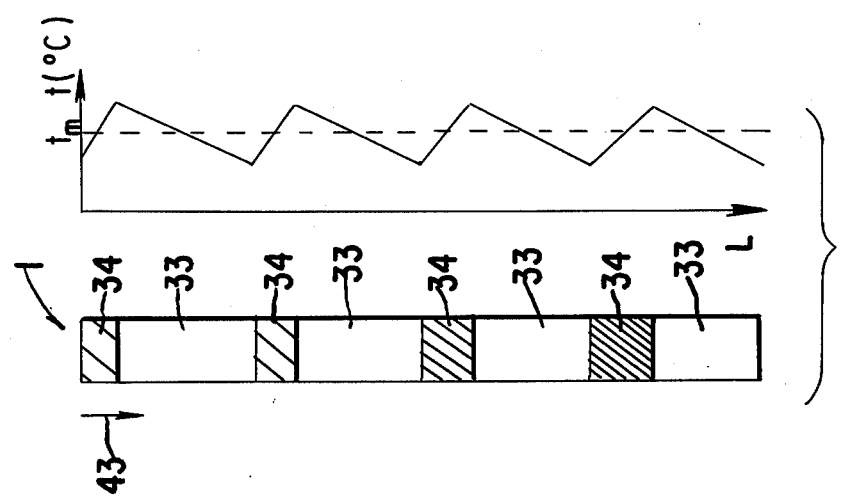
FIG. 5 is a cross-section of another embodiment of the reaction of the invention wherein empty spaces are between successively longer mixing sections of the same hydraulic diameter.
Figure 4:
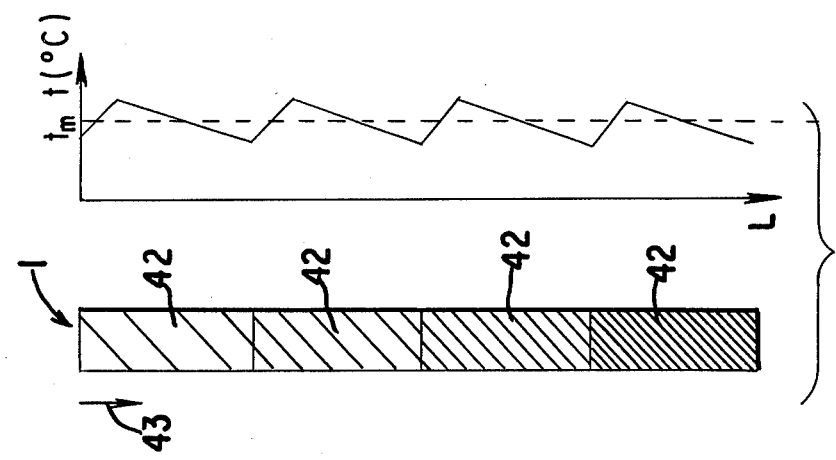
FIG. 4 is a cross-section of a reactor with successive mixing sections of graded hydraulic diameter.

An embodiment of the present invention will now be more particularly described by way of example with reference to the figures of the accompanying drawings, in which:

FIG. 1 is a diagrammatic flow chart indicating two reactors, pumps and the material flow;

FIG. 2 is a diagrammatic flow chart indicating the two reactors of FIG. 1 and a booster reactor and pumps and the material flow;

FIG. 3 is a diagrammatic flow chart indicating three reactors together with intermediate tanks, valves and pumps and the material flow;

FIG. 4 is a cross-section of a reaction tube with successive mixing sections of graded hydraulic diameter;

FIG. 5 is a cross-section of a reaction tube with alternately successively mixing sections and empty tube lengths, and FIG. 6 is a cross-section of a reaction tube with mixing sections of graded hydraulic diameter and accordingly constant ratio of mixer to empty tube length.

In FIG. 1 of the drawings, there is shown a reactor system according to the invention consisting of at least two reactors 1 and 2, which are so interconnected that the systemic gaseous and liquid phases are in counterflow to each other but at the same time pass in parallel flow through the individual reactors. This in a sense combines the advantages of both counterflow and parallel flow operating modes. This circuit connection then prevents a reaction between the concentrated reactants first entering the reactor system, namely, between the charge mixture 4 and ozonic gas 5. For this reason alone, the reaction heat is better distributed in the reactors, and temperature jumps are avoided. Moreover, because parallel flow conditions prevail within the individual reactors, a relatively high gas velocity is feasible. Therefore, the reactors can to a corresponding degree be small dimensioned. Thus, the use of an inexpensive mixture of ozone with air at a low ozone concentration, in particular 0.1% to 1% of ozone, is feasible.

The reactors 1 and 2 are preferably equipped with the aforesaid static mixers. These involve, for example, the static mixers with mixing elements consisting of grooved laminations and fitted together with formation of intersecting open channels, and/or the static mixers with alternately right-handed and left-handed spirals placed one behind the other.

It is the function of the mixing elements to bring the three phases (organic phase, water and ozone-containing gas) in contact with one another, that is, to emulsify the two liquid phases very finely and to mix the gas phase with this emulsion intensively. This is effected in the mixers by reduction of the drop size and redistribution thereof, i.e., by creation of ever new surfaces, combined with multiple deflection of the gas stream.

According to the flow chart of FIG. 1, the charge mixture 4, consisting of the organic phase and water in a finely distributed state, is fed to reactor 1, while fresh ozonic gas 5 is fed to reactor 2. In the exemplified embodiment in reactor 1 primarily, the ozonic waste gas 8 from reactor 2 is nearly quantitatively reacted with a fresh charge mixture. In reactor 2, on the other hand, the ozonization of the partially reacted charge mixture 4 from reactor 1 with fresh ozonic gas is continued to its conclusion.

The pumps 13 in lines 9, 10, 11 and 12 are provided for transport of liquid products. Waste gas 6 is removed from the system. Static mixers 34 and free spaces 33 are present in the reactors.

In FIG. 2 a reactor system with a booster reactor 3 is shown. Booster reactor 3 makes for a more flexible operating mode and in any given case buffers fluctuations and breakdowns. As in the case of reactors 1 and 2, the reactants pass through reactor 3 in a parallel flow but reactor 3 is connected to the other reactors in counter-flow. With this operating mode the main reaction occurs in reactor 2. In reactor 1 the residual ozone is washed out of the waste gas 8 of reactor 2 with fresh charge mixture 4. In reactor 3, however, the unreacted charge mixture from reactor 2 is completely reacted with fresh ozonic gas 5. The partially reacted charge mixture from reactor 1 flows into reactor 2 via line 10. The waste gas 6 is removed from the system. The partially reacted ozonic gas from reactor 3 also flows into reactor 2 via line 7. Both reactants are reacted for the most part in reactor 2. Pumps 13 in lines 9, 10, 11 and 12 are provided for the transport of liquid products.

As in the arrangement shown in FIG. 1, static mixers 34 can be present in the reactors in an ordered arrangement with intervening free spaces 33.

With an arrangement as shown in FIG. 3, the charge mixture 4 is fed directly into reactor 1, whereas the ozonic gas 5 is separated into two currents 14 and 15 in such a way that larger current 14 is fed into reactor 2 and the smaller current 15 into reactor 3. Waste gas 16 from reactor 3 is fed to reactor 1.

With an apparatus as shown in FIG. 3, the liquid and gaseous phases of reactants and reaction products are first separated in appropriately post-staged tanks 17 to 19. Corresponding waste gas currents are designated by the upward-pointed arrows 20 to 22. The liquid phase flows downward to intermediate tanks 26 to 28 via lock-up valves 23 to 25, and to the next reactor and/or outlet 32 via pumps 29 to 31. It should be noted that the charge mixture and ozonic gas can be added also at the head of the individual reactors. Both the reactants, as shown in FIGS. 1 and 2, accordingly flow in the reactor from the top down to the bottom.

In the reactor system shown in FIG. 3 the biggest ozone reaction takes place in reactor 2, and its waste gas 21 is practically ozone free. In reactor 3 the last ozonizable traces of the charge mixture are ozonized by means of fresh ozonic gas (line 15), so that the charge mixture is completely ozonized. Waste gas 22 from reactor 3 still contains a considerable amount of ozone, which is washed out in reactor 1 with fresh charge mixture.

As in the arrangement shown in FIGS. 1 and 2, static mixers 34 can be present in the reactors in an ordered arrangement with intervening free spaces 33.

The subsequent hydrolytic-oxidative scission is carried out with relatively minor amounts of air. About 10% to 25% of the air volume required for ozonization is used in this step.

As is well known, ozone traces promote the above-mentioned scission. Therefore, the advantage of an arrangement such as is shown in FIG. 3 is that the gas volume in reactor 2 can be so adjusted that waste gas is developed to the extent required for a subsequent hydrolytic-oxidative scission. Furthermore, the ozone reaction in reactor 2 can be so controlled that waste gas 21 still contains the amount of ozone required for hydrolytic-oxidative scission.

The reactors of the systems according to FIGS. 1, 2 and 3 are preferably equipped with the above-mentioned static or stationary mixing parts. In this case, they are, e.g., static mixers 34 having corrugated lamella elements joined to produce intersecting open channels, and/or static mixers having consecutively arranged, alternately right- and left-hand helix turns. Reactor 3 in FIG. 2, however, is a filter bed column. Such type of mixing device, therefore, is also usable.

In all three reactors 1, indicated in FIGS. 4 to 6, it has been assumed that the material transport inside the reactor occurs downward in the direction of arrow 43. To the right of each reactor 1, the curve of the temperature t in °C. (inside the reactor elements) over the length L of the reactor has been plotted in a diagram.

The reactor 1 according to FIG. 4 consists of mixers 42 of approximately equal length, equipped with mixing elements whose hydraulic diameters become narrower and narrower graded from mixer to mixer in the direction of arrow 43. Evidently it can thereby be achieved that despite a slightly fluctuating temperature t to a mean temperature $t_m$ can be maintained. According to the invention, the mixers 42 are selected and arranged so that the maxima and minima of the temperature t lie within a range in which a premature ozonide splitting does not yet occur but the reaction is checked by heat removal which is also not too intense.

In the reactor 1 according to FIG. 5, mixers 34 and empty tube spaces 33 follow each other alternately. Here the temperature curve is controlled within the given limits by having an equalization of the reaction heat $Q_R$ being released and heat $Q_A$ removed occur in a unit of volume in such a way that a mixing section 34 with a ratio $Q_R/Q_A > 1$ is followed by an empty tube space 33 with $Q_R/Q_A > 1$. The ratio of mixer length to empty tube length is varied in arrow direction 43 (i.e., in the direction of the reaction flow) in favor of the mixing section, so as to take account of the increasingly more intensive mixing which gradually becomes necessary due to the increasing viscosity and the decreasing conversion increment. Again, the temperature plot of the reactor is indicated alongside.

According to FIG. 6, the increasingly more intense mixing can alternatively be achieved if, as the reaction proceeds (in arrow direction 43), the hydraulic diameter of the filling bodies in the mixers 46 is reduced so that per unit volume of the mixers 46, the conversion increment becomes the same and the ratio of mixing section 46 to empty section 33 remains unchanged. Again, the temperature plot of the reactor is indicated alongside.

The static mixers or filling bodies in the apparatus of the invention are designed and arranged so that they form a stable emulsion from the charge mixture of the aqueous and the organic phase, mixing this emulsion thoroughly with the ozone-containing gas and continuously creating new surfaces. Therefore, consumed ozone is replenished at the liquid surface and the phase transition or, respectively, the diffusion of ozone into unreacted organic phase is furthered. The controlled arrangement of the mixing elements also has the result that a sudden mixing and hence a spontaneous reaction cannot take place. Therefore, the reaction proceeds uniformly in the individual reactors over the entire section although the viscosity of the liquid phase increases with the degree of ozonization.

By the use of static mixers or filling bodies and their arrangement and distribution according to the invention in the reactors, there is achieved at relatively little cost a uniform heat removal at low temperature in the reactors and hence high technical safety.

Through the present invention it thus becomes possible to attain a practically quantitative conversion of the ozonizing charge mixture with a minor, not more than negligible excess of ozone. This is possible because the speed of the present ozonization reaction becomes a key function of ozone diffusion from the gaseous to the liquid phase. The present invention provides the means for ensuring that the liquid reactant phase affords not only a large but a constantly renewable surface.

These mixing means of the invention produce an intensive mixture of both phases to the extent that each reactant is consumed. The factors to be considered here are that ozonic gas is available only at a concentration of 0.5 to 2.5 volume percent and a precompression usually of less than 2 bar, that the liquid-to-gaseous phase volumic ratio (according to the process according to the invention) is about 1:1,500 to 4,000 and that the viscosity increases with a rising degree of ozonization. Another notable factor is that the reaction heat on ozonization amounts to about 2,000 kcal/kg ozone, but the reactor temperature must be limited to 10° to 50° C. so that the oxonide scission is not prematurely started.

The present invention thus provides a process for the continuous ozonization of a long-chain, olefinically unsaturated organic compound of about 10 to 24 carbon atoms chain length, wherein:

(a) a fresh charge mixture to be ozonized, consisting essentially of said unsaturated organic compound and 2 to 49 weight percent, based on the weight of said unsaturated organic compound, of water, is reacted in parallel flow with ozonic gas, which was previously used for ozonizing a previously partially ozonized charge mixture, and (b) simultaneously a previously partially ozonized charge mixture is reacted in parallel flow with fresh ozonic gas consisting essentially of air with a concentration of 0.1 to 2.5 volume percent, more particularly 0.1 to 1 volume percent, ozone, the parallel flow reaction temperatures being at about 10° to 50° C. and the liquid-to-gaseous phase volumic ratio in the ozonization process being about 1:1,500 to 4,000. Examples of long-chain olefinically unsaturated organic compounds which can be ozonized by the present process are olefins and fatty carboxylic acids or acid derivatives, such as esters, amides, etc. A reaction solvent as, for example, an organic acid or alcohol, can be added together with the charge mixture. Such reaction solvents as, for example, organic carboxylic acids, can readily be recovered from the ozonization process by standard separation techniques, such as distillation. The amounts of the reactive solvents to be added to the charge mixture to be ozonized can be determined through routine experimentation.

In an especially advantageous embodiment of the invention, the reaction is controlled and promoted in the reactor by an arrangement of mixing elements or filter beds so ordered that the reaction heat is not produced suddenly in a small space but is uniformly distributed over the entire reactor space. The result is that reaction heat can be removed by uniform water evaporation (without any reactor temperature- and/or pressure fluctuations). According to the invention, a quasi-isothermal operating mode is, therefore, feasible.

A further way of avoiding local overheating is to recycle the run-off liquid back to the reactor head. The static or stationary mixing elements or filter beds in the reactors according to the invention are so constructed and arranged that they produce a stable emulsion from the charge mixture of hydrous and organic phases and that they mix said emulsion well with the ozonic gas and constantly produce new surfaces. In this way, the ozone consumed on the liquid surface is supplemented, and a phase transition and/or ozone diffusion to the unreacted organic phase is promoted. Another result of the ordered arrangement of mixing elements is that a sudden mixing and with it a spontaneous reaction cannot occur. Therefore, a uniform reaction flow is produced over the entire reaction route through the individual reactors even though the liquid phase viscosity rises with the degree of ozonization.

The process according to the invention and the corresponding reaction apparatus are of advantage also because the new reactor system allows for a quantitative reaction without any expensive counterflow reactors. Residual ozone is developed only to a negligible extent. A high reaction velocity is feasible because of the intensive gas/liquid contact. The liquid hold-up in the individual reactors is thereby kept at a very low level. In spite of the use of a relatively minor amount of water, a stable water-in-oil emulsion is produced because of the intensive type of mixing. Because of the relatively minor amounts of water used, reprocessing costs and production losses are reduced relative to the corresponding state of the art processes. The waste water problem is also allieviated. Finally, if nested tube reactors are used, then an average reaction temperature can be set at will by additionally installed indirect heating and/or cooling means.

By using static mixing parts and/or filter beds in an ordered arrangement in the reactors, there is obtained a uniform heat removal at low reactor temperatures and with it a high industrial safety margin, with relatively little expense. The volume of water used according to the invention amounts at least to that required for in-situ removal of reaction enthalpy, plus an excess for reducing the viscosity of the ozonized product. No more water is used, however, than is required anyway for the subsequent scission. This makes it possible to limit the amount of water required, to 2% to 49% of the charge mixture (organic phase). Thus, the function of the water is substantially to trap the exothermal heat of reaction, to control the temperature in the individual reactors and to lower the viscosity of the reaction product, particularly toward the end of the reaction.

The final accomplishment of the invention is that relatively small-sized reactors can be utilized for ozonization purposes. The result produced by using static mixing components and/or special filter beds with the above-mentioned ordered arrangement in the individual reactors is that the liquid hold-up in the individual reactors is kept very low. This is of great advantage for safety reasons, because of the well known fact that ozonized products tend to an explosive disintegration.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A continuous process for the ozonization of a higher molecular weight olefinically unsaturated organic compound, which consists essentially of the steps of:
   (a) continuously feeding a fresh charge mixture of the unsaturated organic compound, said compound having a boiling point at normal pressure of at least 50° C., which mixture contains 2 to 49 weight percent of water, relative to the weight of said unsaturated organic compound, into parallel flow in a confined space with the ozone-containing off gas from a previous ozonization wherein said unsaturated organic compound and said ozone-containing off gas are intimately mixed continuously throughout their parallel flow together and wherein the partially ozonized charge produced is optionally similarly reacted with a further charge of ozone-containing gas in one or more additional parallel flow reactions,
   (b) continuously withdrawing from step (a) a partially ozonized charge and gas substantially free of ozone,
   (c) continuously feeding said partially ozonized charge containing water from step (b) into parallel flow in a confined space with ozone-containing gas and intimately mixing said partially ozonized charge and said ozone-containing gas continuously throughout their parallel flow together,
   (d) continuously passing ozone-containing gas containing 0.1 to 1 volume percent ozone into step (c),
   (e) continuously withdrawing the ozonized charge containing none-to-sufficient water for hydrolysis of the ozonide and a partially depleted ozone-containing off gas,
   (f) continuously separating said gas, and cycling it to step (a), and
   (g) continuously recovering an ozonide of said higher molecular weight olefinically unsaturated organic compound, and
wherein said parallel flow reactions in steps (a) and (c) are conducted at a predetermined temperature of from 10° to 50° C. and at a pressure sufficient that substantially all the heat of reaction is removed by evaporation of the water present.

2. The process of claim 1, wherein there is added to the fresh charge mixture a reactive solvent which converts the ozonides produced to hydroperoxides.

3. The process of claim 2, wherein the reactive solvent is a member selected from the group consisting of an organic acid and an organic alcohol.

4. The process of claim 1, wherein the unsaturated organic compound is a member selected from the group consisting of olefins and fatty carboxylic acids.

5. The process of claim 4, wherein the carboxylic acids are selected from the group consisting of oleic acid and linoleic acid.

6. The process of claim 1, wherein there are present in the individual parallel flow reaction paths static mixing components of such a type and arrangement that an intimate mixture of reactants, water and reaction products is ensured, which mixture is intensified with an increasing degree of ozonization.

7. The process of claim 6, wherein the individual parallel flow reactions are conducted in nested tube reactors.

8. The process of claim 6, wherein said static mixing components have varied hydraulic diameters and said static mixing components of varied hydraulic diameters are arranged whereby a reduced hydraulic diameter occurs in the direction of the parallel flow.

9. The process of claim 8, wherein said static mixing components of varied hydraulic diameters arranged whereby a reduced hydraulic diameter occurs in the direction of the parallel flow are separated by empty spaces.

10. The process of claim 1, wherein there are present in the individual parallel flow reaction paths filter beds or a combination of static mixing components and filter beds.

11. The process of claim 1, wherein the temperature of the individual parallel flow reactions are regulated by a cooling and/or heating jacket.

* * * * *

UNITED STATES PATENT AND TRADEMARK OFFICE
CERTIFICATE OF CORRECTION

PATENT NO. : 4,185,025
DATED : January 22, 1980
INVENTOR(S) : FRANZ-JOSEF CARDUCK et al It is certified that error appears in the above—identified patent and that said Letters Patent is hereby corrected as shown below:

In the Heading, Item "[30]" under the line starting

"Dec. 7, 1977" please insert

-- March 29, 1977 [DE] Fed. Rep. of Germany.....2713863--

Col. 1, line 19, Page 2, line 12, "ozoning" should be

--ozonizing--

Col. 1, line 26, Page 2, line 18, "of" should be --or--

Col. 11, line 22, Page 25, line 15, "$Q_R/Q_A>1$" should be

--$Q_R/Q_A<1$--

Signed and Sealed this

Tenth Day of August 1982

[SEAL]

Attest:

GERALD J. MOSSINGHOFF

Attesting Officer       Commissioner of Patents and Trademarks